United States Patent
Deghionno (10) Patent No.: US 11,964,078 B2
(45) Date of Patent: Apr. 23, 2024

(54) PUSH-BUTTON ACTIVATED SNIFFING CAP

(71) Applicant: Milo Jack Deghionno, Encinitas, CA (US)

(72) Inventor: Milo Jack Deghionno, Encinitas, CA (US)

(*) Notice: Subject to any disclaimer, the term of this patent is extended or adjusted under 35 U.S.C. 154(b) by 0 days.

(21) Appl. No.: 18/196,406

(22) Filed: May 11, 2023

(65) Prior Publication Data

US 2023/0364295 A1    Nov. 16, 2023

Related U.S. Application Data (60) Provisional application No. 63/340,858, filed on May 11, 2022.

(51) Int. Cl.
*A61L 9/14* (2006.01)

(52) U.S. Cl.
CPC .......... *A61L 9/14* (2013.01); *A61L 2209/134* (2013.01)

(58) Field of Classification Search
None
See application file for complete search history.

(56) References Cited

U.S. PATENT DOCUMENTS

| | | | |
|---|---|---|---|
| 2002/0074365 A1 | 6/2002 | Young | |
| 2007/0060868 A1 | 3/2007 | Tsutsui | |
| 2014/0124964 A1 | 5/2014 | Mayor Sans et al. | |
| 2015/0112161 A1* | 4/2015 | Mills | A61B 5/0875 600/303 |

FOREIGN PATENT DOCUMENTS

| | | | | |
|---|---|---|---|---|
| DE | 102006050652 A1 * | 4/2008 | .......... | A01M 1/2055 |
| WO | 2022/044514 A1 | 3/2022 | | |

OTHER PUBLICATIONS

DE102006050652A1—translated document (Year: 2006).*
International Search Report and Written Opinion dated Aug. 15, 2023 in corresponding International Application No. PCT/US23/21952; 6 pages.
"Don't let a spill ruin your night", Super Sniffer, Nov. 7, 2022, https://web.archive.org/web/20221107081909/https://www.thesupersniffer.com/.

* cited by examiner

*Primary Examiner* — Jelitza M Perez
(74) *Attorney, Agent, or Firm* — Plager Schack LLP; Mark H. Plager; Kara Verryt (57) ABSTRACT

A sniffing cap for an aroma bottle providing for regulated access to an aroma within the aroma bottle may include a cap body having a top cap portion, a bottom cap portion, and a push button positioned between the top cap portion and the bottom cap portion. The top cap portion may include at least one nozzle opening designed to be placed against a user's nostril and air vents extending through a side surface of the top cap portion. The bottom cap portion may be attached to the top cap portion and may include a dual section airflow tube extending therefrom. The push button may include a push button body configured to engage and disengage with channels in the cap body, thus regulating flow of air into and scent out of the aroma bottle.

9 Claims, 11 Drawing Sheets

PUSH-BUTTON ACTIVATED SNIFFING CAP

RELATED APPLICATION

This application claims priority to provisional patent application U.S. Ser. No. 63/340,858 filed on May 11, 2022, the entire contents of which is herein incorporated by reference.

BACKGROUND

The embodiments described herein relate generally to aroma containers and, more particularly, to a push-button activated, spill-proof sniffing cap for aroma bottles.

Repeatedly accessing the contents of an aroma bottle conventionally requires removing and replacing the cap onto the bottle. This process generally requires two hands and leaves room for spillage to occur. While other venting caps also exist, these generally allow for sniffing, but do not prevent evaporation or spillage, as the vents or holes in the existing caps remain open.

Therefore, what is needed is a sniffing cap for an aroma bottle, wherein the sniffing cap is suitable for single-hand use and allows a user to regulate access to the contents, thus preventing unnecessary evaporation and accidental spillage.

SUMMARY

Some embodiments of the present disclosure include a sniffing cap for an aroma bottle providing for regulated access to an aroma within the aroma bottle may include a cap body having a top cap portion, a bottom cap portion, and a push button positioned between the top cap portion and the bottom cap portion. The top cap portion may include at least one nozzle opening designed to be placed against a user's nostril and air vents extending through a side surface of the top cap portion. The bottom cap portion may be attached to the top cap portion and may include a dual section airflow tube extending therefrom. The push button may include a push button body configured to engage and disengage with channels in the cap body, thus regulating flow of air into and scent out of the aroma bottle.

BRIEF DESCRIPTION OF THE FIGURES

The detailed description of some embodiments of the invention is made below with reference to the accompanying figures, wherein like numerals represent corresponding parts of the figures.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used as a sniffing cap for an aroma bottle and may comprise the following elements. This list of possible constituent elements is intended to be exemplary only, and it is not intended that this list be used to limit the device of the present application to just these elements. Persons having ordinary skill in the art relevant to the present disclosure may understand there to be equivalent elements that may be substituted within the present disclosure without changing the essential function or operation of the device.

The various elements of the present disclosure may be related in the following exemplary fashion. It is not intended to limit the scope or nature of the relationships between the various elements, and the following examples are presented as illustrative examples only.

By way of example, and referring to FIGS. 1-18, some embodiments of the present disclosure include a sniffing cap for an aroma bottle 24, the sniffing cap comprising a cap body including a top cap portion attached to a bottom cap portion, wherein the top cap portion comprises at least one nozzle opening designed to be placed against a user's nostril for sniffing and at least one air vent extending through a side surface of the top cap portion; a push button slidably engaged with the top cap portion, the push button configured to, on demand, prevent and permit air flow into the aroma bottle and scent flow out of the aroma bottle; and the bottom cap portion is configured to removably engage with the aroma bottle 24, the bottom cap portion including an optional dual-section air flow tube extending therefrom, wherein a first section of the air flow tube is configured to permit air flow into the aroma bottle and a second section of the air flow tube is configured to permit scent flow out of the aroma bottle when the push-button is activated. When the push-button is pushed into the top portion of the cap (i.e., activated), the push-button may allow for airflow into the vents, through the cap, and into the aroma bottle, causing scent 34B to flow up through the cap and out of the nozzle opening. When the push-button is released, the push-button may block flow of air into and flow of scent out of the aroma bottle.

Figure 8:
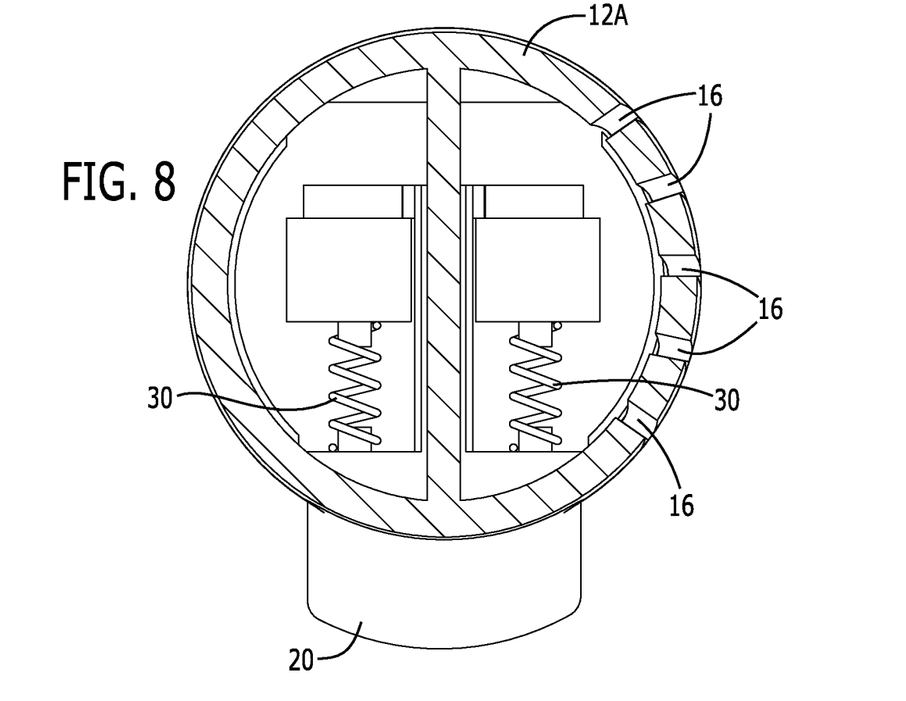
FIG. 8 is a cross-sectional view of one embodiment of the present disclosure, taken along line 8-8 in FIG. 3.
Figure 9:
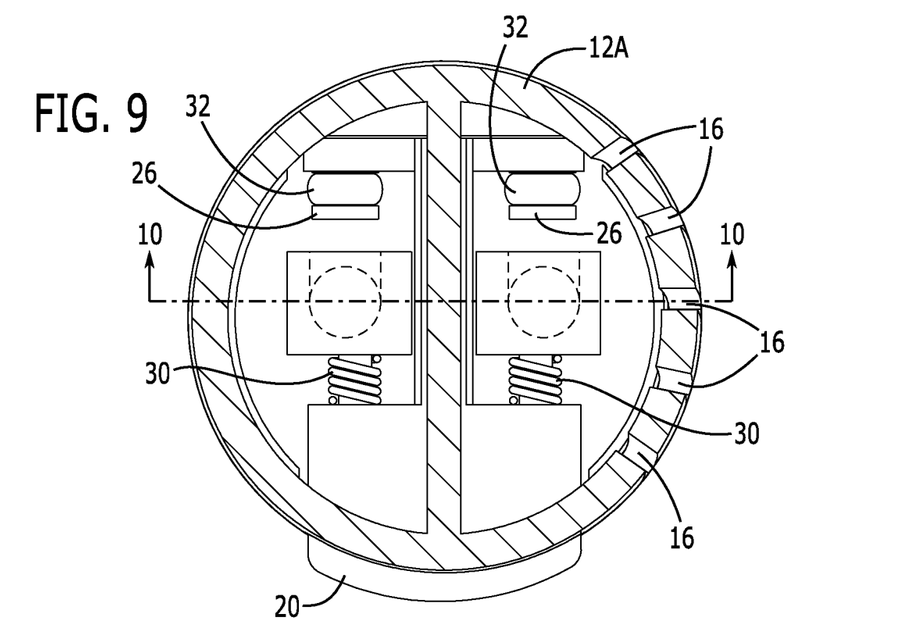
FIG. 9 is a cross-sectional view, similar to FIG. 8, showing activation of an embodiment of the push-button of the present disclosure.
Figure 10:
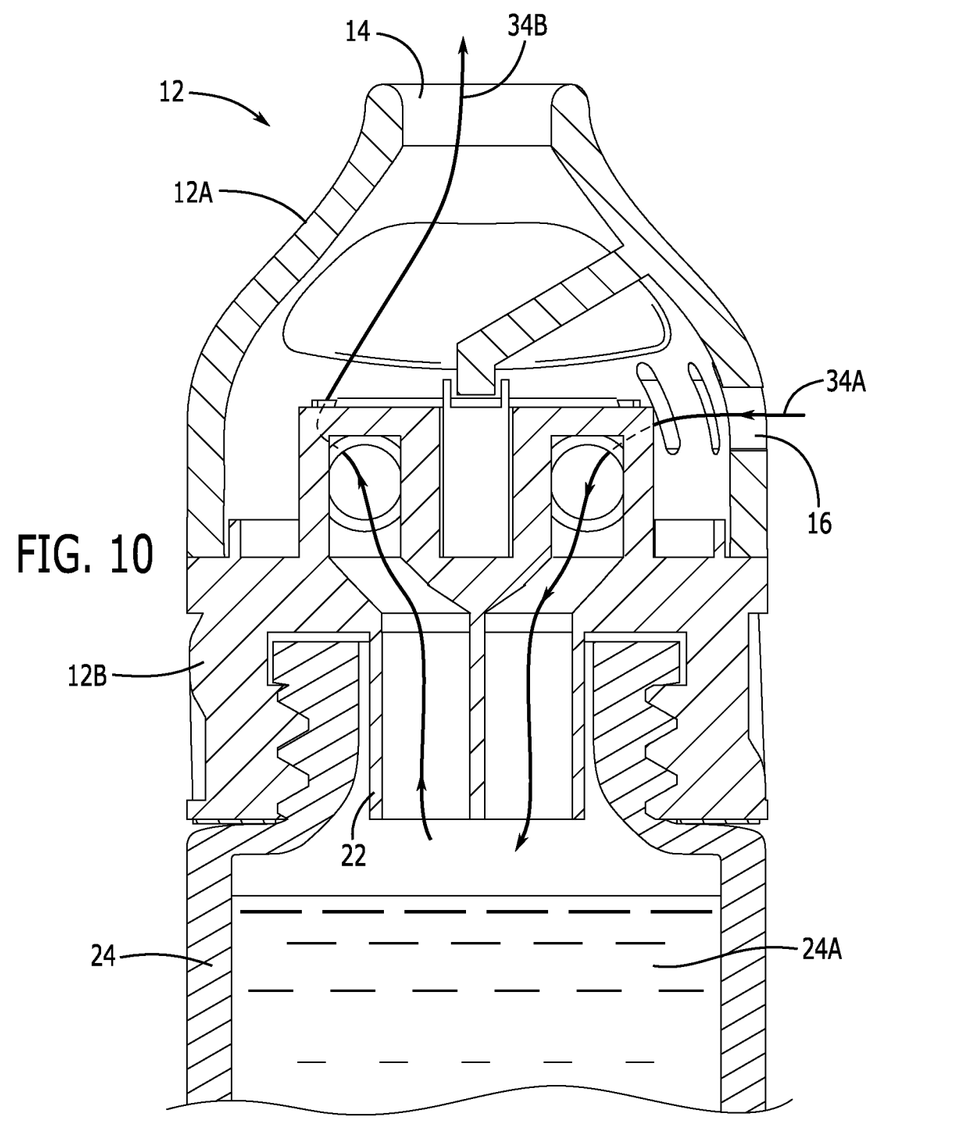
FIG. 10 is a vertical cross-sectional view of one embodiment of the present disclosure, taken along line 10-10 in FIG. 9.

More specifically, and as shown in FIGS. 1-10, the sniffing cap 10 may comprise a cap body 12 comprising a top cap portion 12A attached to a bottom cap portion 12B, wherein the top portion 12A includes the nozzle opening 14 and at least one air vent 16, such as a plurality of air vents 16, extending through a side surface of the top cap portion 12A. As shown in the Figures, and particularly in FIG. 5, the top portion 12A of the cap body 12 may comprise an outer wall, such as a substantially dome-shaped outer wall, with a nozzle opening 14 extending therethrough. An interior of the top portion 12A may comprise a top interior region, a middle interior region, and a bottom interior region. A partition within an interior of the top portion 12A may extend at an angle from an interior wall within the top interior region to a central area of the middle interior region, thus dividing the interior of the top portion 12A, as shown in FIG. 10. As such, the nozzle opening 14 may be separated from the air vents 16, meaning that air may not flow from the air vents 16 through the top portion 12A and directly to the nozzle opening 16. The top portion 12A may further comprise a push button opening extending therethrough, wherein the push button opening may be positioned in the bottom region of the top portion 12A and, thus, vertically below the partition. The push button opening may be sized to accommodate a push button 20 slidably mounted therein.

As shown in the Figures, the push button 20 may comprise a button head designed to extend outward from the top portion 12A and a button body extending from the button head, the button body designed to be positioned within the bottom interior region of the top portion 12A. As shown in, for example, FIG. 6, the push button body may comprise a narrow stem extending from the push button head, wherein the narrow stem may comprise an upper edge with outer raised walls, defining a push button slot 20A. When in use, the push button slot 20A may hug a bottom portion of the partition and, thus, may be sized to accommodate positioning of the bottom portion of the partition therein. A pair of tabs may each extend substantially perpendicularly outward from a distal end of the stem, wherein each of the pair of tabs may be substantially parallel with a surface of the push button head proximate to the stem. Each of the pair of tabs may comprise a slotted peg 26 extending outward therefrom and toward the button head. As shown in FIG. 9, an O-ring 32 may encircle a shaft of the slotted peg 26 such that the O-ring 32 is positioned between a head of the slotted peg 26 and the tab.

Figure 2:
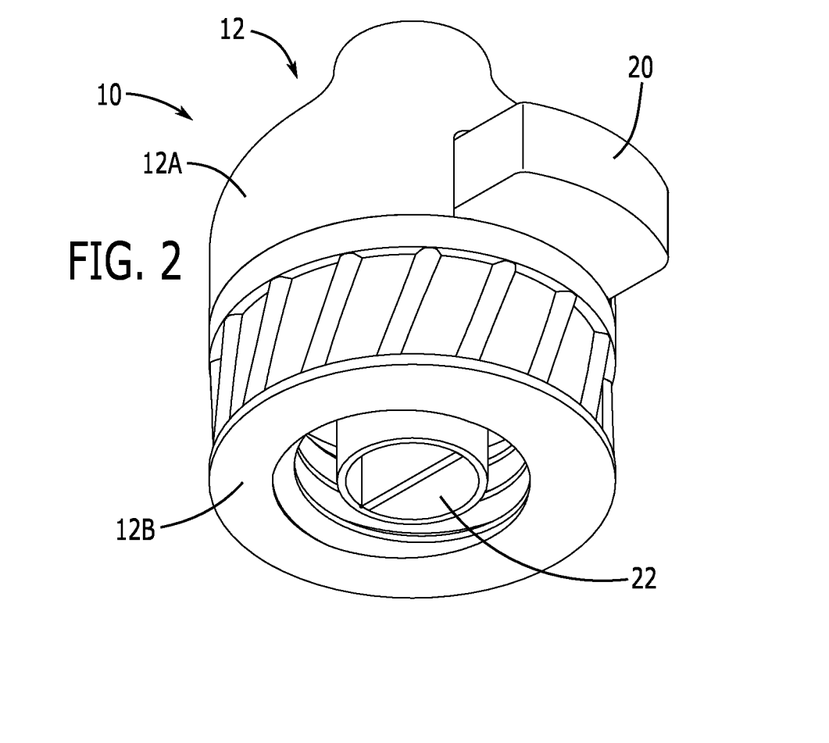
FIG. 2 is a bottom perspective view of one embodiment of the present disclosure.
Figure 3:
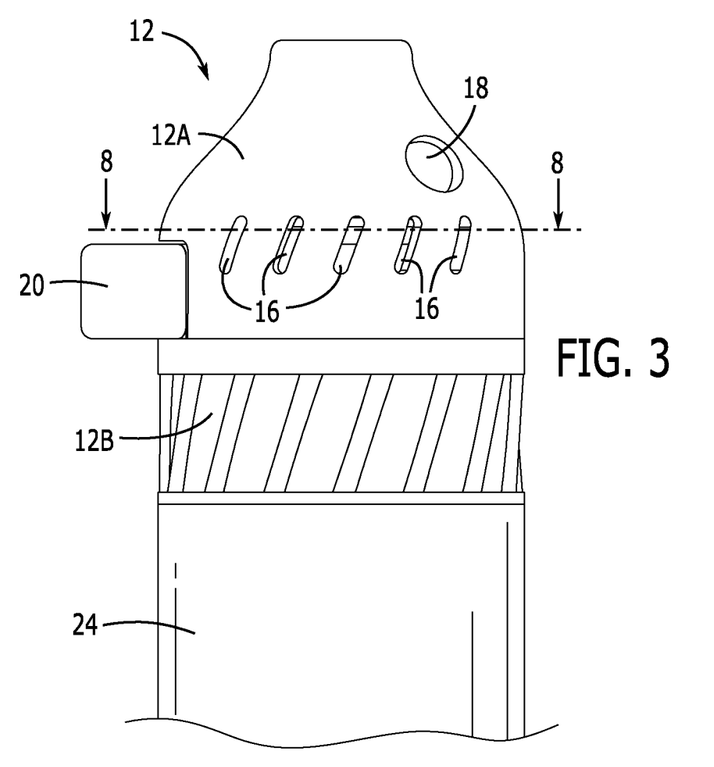
FIG. 3 is a side elevation view of one embodiment off the present disclosure.
Figure 4:
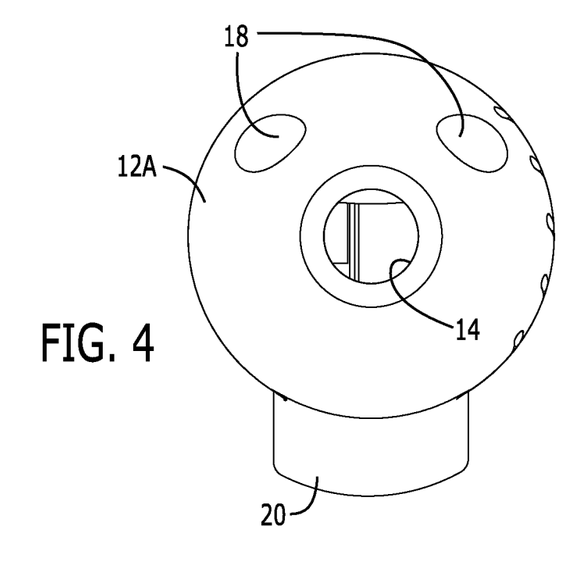
FIG. 4 is a top plan view of one embodiment of the present disclosure.
Figure 5:
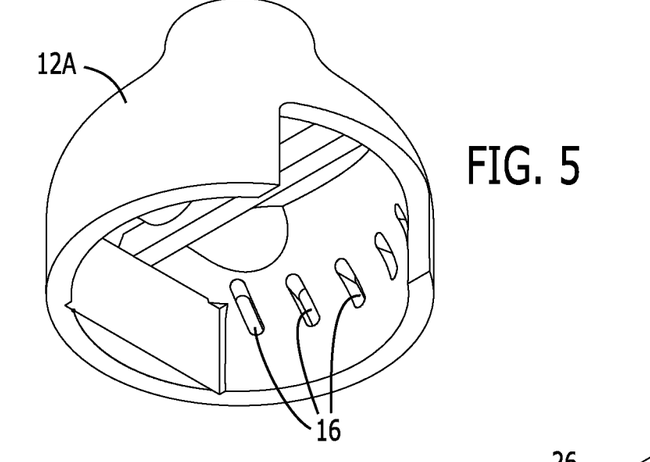
FIG. 5 is a bottom perspective view of a top portion of one embodiment of the present disclosure.
Figure 6:
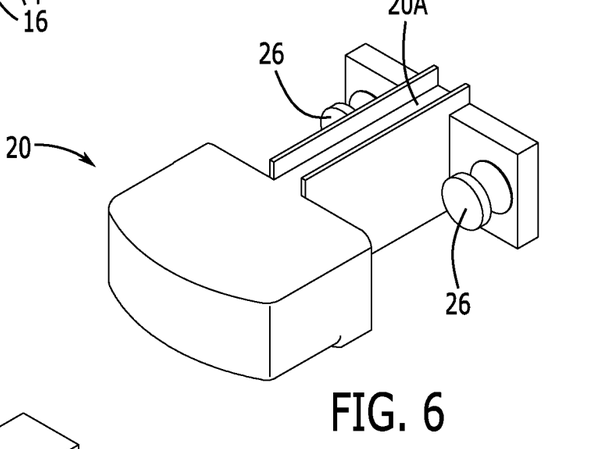
FIG. 6 is a top perspective view of one embodiment of a component of the present disclosure.
Figure 7:
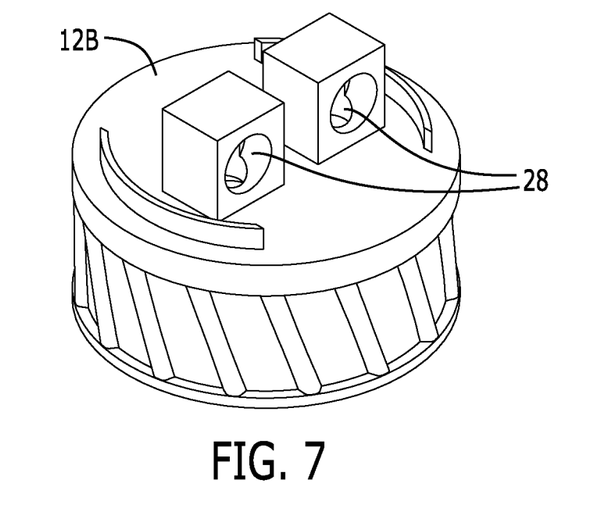
FIG. 7 is a top perspective view of a bottom portion of one embodiment of the present disclosure.

As shown in FIGS. 2 and 7, the bottom portion 12B of the cap body 12 may comprise a substantially cylindrical body with a first open end and a second closed end. As shown in FIG. 2, the open end may comprise interior threads designed to removably engage with threads on the neck of an aroma bottle 24 and a dual section airflow tube 22 concentrically positioned within the open end and extending from the interior surface of the closed end of the bottom portion 12B. A gasket 52 may be positioned at a top edge of the threads and adjacent to an interior surface of the closed end to allow for a sealed connection when the bottom portion is engaged with the aroma bottle 24. The dual section airflow tube 22 may comprise a tube with at least one divider extending the length thereof, thus dividing the tube 22 into two airflow portions. In some embodiments, the dual section airflow tube 22 may comprise a plurality of dividers, thus dividing the tube 22 into multiple airflow portions. In yet further embodiments, the dual section airflow tube 22 may be shortened, lengthened, or removed, if desired without significantly impacting the overall function of the device. As shown in FIG. 7, the closed end of the bottom portion 12B may comprise a pair of valve protrusions extending upward therefrom. Each of the valve protrusions may be positioned on a respective opening in the closed end, wherein a first opening aligns with a first half of the dual section airflow tube 22 and a second opening aligns with a second half of the dual section airflow tube 22. Each valve protrusion may be substantially square or rectangular shaped with a channel 28 extending through two parallel sides thereof and an opening the bottom surface thereof, such that the exterior of the closed end is in fluid communication with the dual section airflow tube 22.

The channel 28 extending through each of the valve protrusions may be sized to accommodate insertion of a respective slotted peg 26 with O-ring 32 therein. Thus, in embodiments, when the top portion 12A is attached to the bottom portion 12B, the push button 20 may be sandwiched between the top portions 12A and the bottom portion 12B of the cap body 12, wherein the stem of the push button 20 may be positioned between the pair of valve protrusions and movement of the push button 20 causes the slotted pegs 26 to engage and disengage with the channels 28 in the valve protrusions. As such, when the slotted pegs 26 with the attached O-rings 32 are inserted into channel 28, a valve that controls airflow into and out of the device may be created.

The sniffing cap device 10 of the present disclosure may further comprise a pair of springs 30, wherein each spring 30 is positioned between an edge of the valve protrusion on the closed end of the bottom portion 12B and the push button head. More specifically, as shown in FIG. 8, the springs 30 may be positioned on pegs extending from the push button head. As such, the springs 30 force the push button 20 outward with respect to an interior of the cap body 12, causing the slotted pegs 26 and O-rings 32 to engage with the channel 28, thus blocking airflow between the dual section airflow tube 22 and the top portion 12A of the cap body 12. When the push button 20 is pressed toward the interior of the cap body 12, the slotted pegs 26 and O-rings 32 are disengaged from the channels 28, thus allowing airflow between the dual section airflow tube 22 and the top portion 12A of the cap body 12.

Figure 1:
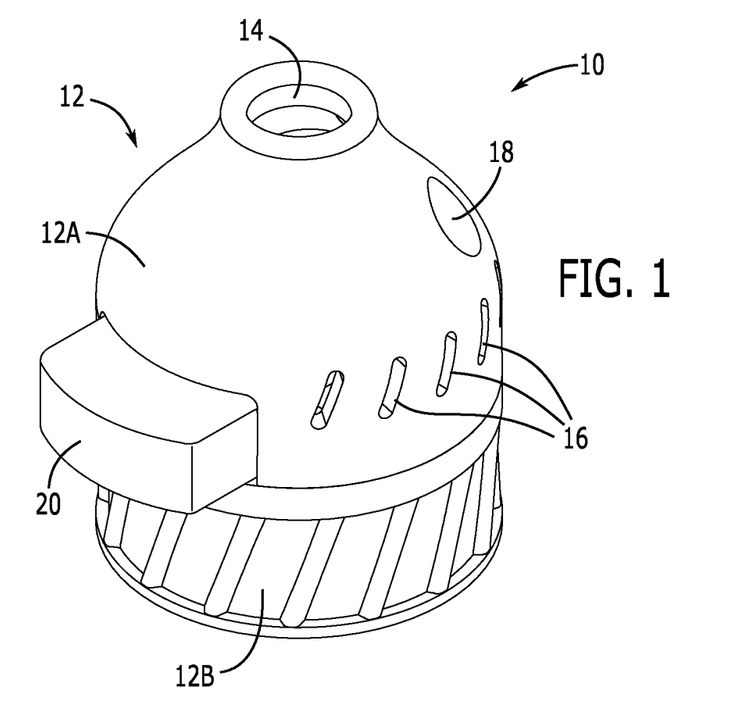
FIG. 1 is a top perspective view of one embodiment of the present disclosure.

As shown in FIG. 1, the sniffing cap 10 of the present disclosure may further and optionally include a necklace channel 18 extending therethrough. The necklace channel 18 may allow for the threading of a necklace, cord, rope, or the like therethrough, such that a user may hang the sniffing cap 10 around his or her neck or from another object, such as a hook.

As shown in FIGS. 1-10, the cap 12 may comprise a single nozzle opening 14, allowing a user to place the device only against a single nostril. However, in other embodiments, the cap may comprise a double-nozzle opening to allow a user to place the sniffing cap against both nostrils.

More specifically, and as shown in FIGS. 11-16, some embodiments of the present disclosure including a sniffing cap with a double nostril cap body 40. Similar to the previously described cap body 12, the double nostril cap body 40 may comprise a top portion 42 and a bottom portion 44.

Figure 13:
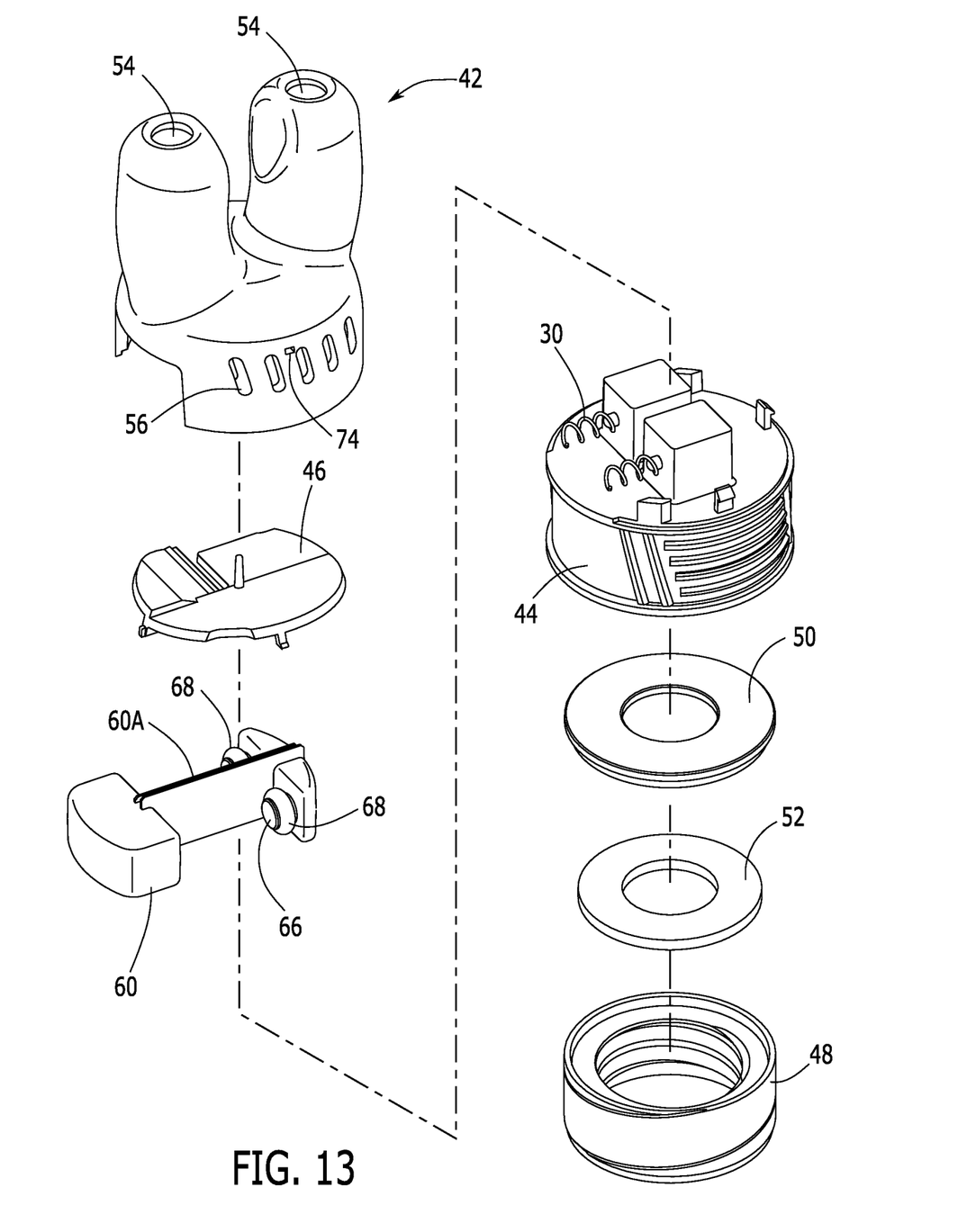
FIG. 13 is an exploded perspective view of one embodiment of the present disclosure.

As shown in FIG. 13, the top portion 42 may comprise an outer wall, such as a substantially dome-shaped outer wall with a pair of nozzle extensions protruding from a surface of the outer wall, wherein each nozzle extension includes a nozzle opening 54 extending therethrough. The nozzle extensions may be spaced a sufficient distance apart such that each nozzle extension may align with a respective nostril on a user during use of the sniffing cap. A surface of the top portion 42, such as a side surface of the outer wall, may include at least one, such as a plurality of, air vents 74 extending therethrough. An interior of the top portion 42 may comprise a top interior region, a middle interior region, and a bottom interior.

Figure 14:
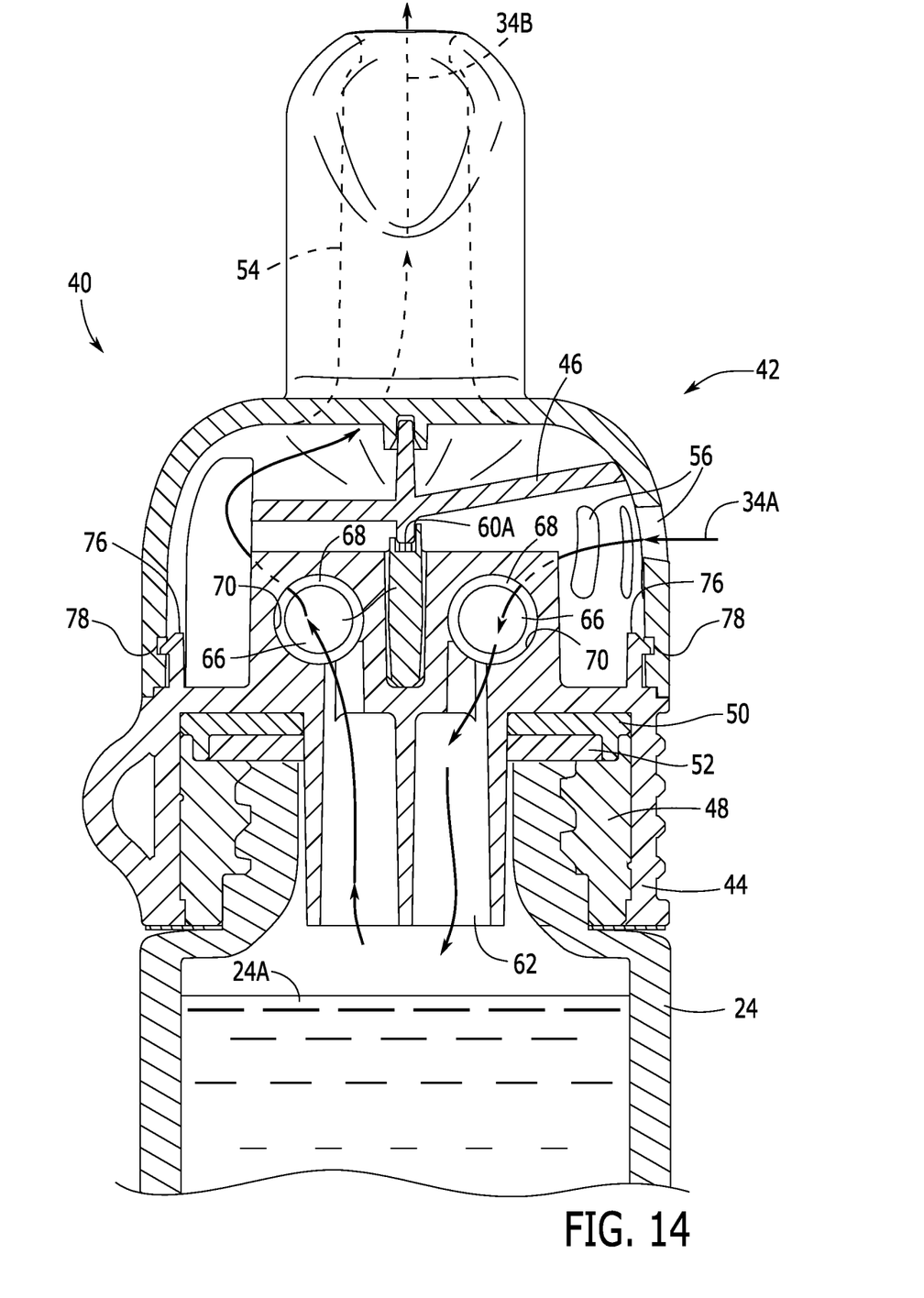
FIG. 14 is a cross-sectional view of one embodiment of the present disclosure, taken along line 14-14 in FIG. 11.
Figure 16:
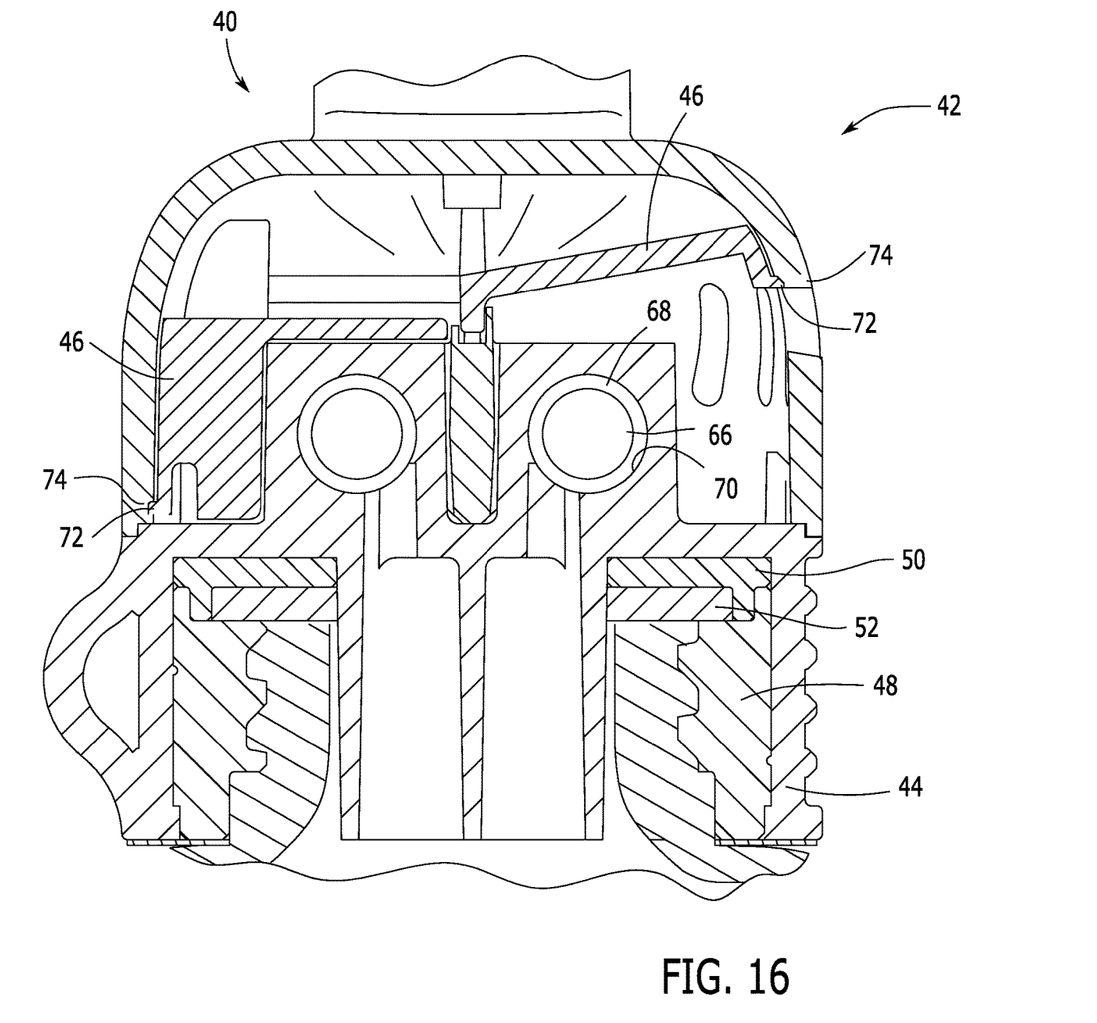
FIG. 16 is a cross-sectional view of one embodiment of the present disclosure, taken along line 16-16 in FIG. 11.

A partition within an interior of the top portion 42 may extend from an interior wall within the top interior region to a central area of the middle interior region, dividing the interior of the top portion 42, as shown in FIG. 14, thus separating the nozzle openings 54 from the air vents 56. In a particular embodiment, the partition may comprise a removable air flow separation wall 46, wherein the airflow separation wall 46 comprises an angled surface that extends from an area above the air vents 56 to a central point of the separation wall 46, a planar surface that extends from the central point of the separation wall 46 toward an interior surface of the cap body 40 opposite the air vents 56, a top extension that extends substantially perpendicularly upward from central point of the separation wall 46, and a central lip extending substantially perpendicularly downward from a central line of the separation wall 46, the central lip running along a width of the separation wall 46. As shown in FIG. 13, the top extension may comprise, for example, a post, wherein the post may be configured to be accommodate within a notch in a top interior surface of the cap body 40, as shown in FIG. 14. As shown in FIG. 16, a distal end of the angled surface of the separation wall 46 may comprise a wall clip 72 extending therefrom, wherein the wall clip 72 may be a tab configured to engage with a wall clip slot 74 extending through the cap body 40 proximate to the air vents 56. The engagement of the top extension and the wall clip 72 with the cap body 40 may help secure the separation wall 46 in place and, thus, the separation wall 46 may be removably attached to the cap body 40. In other embodiments, the separation wall 46 may be formed as an integral part of the cap body 40. In yet further embodiments, the partition may comprise any structure configured to separate the top portion into two separate airflow chambers. For example, the partition may comprise a horizontally oriented wall with air orifices extending therethrough.

The top portion 42 of the cap body 40 may further comprise a push button opening extending therethrough, wherein the push button opening is positioned in the bottom region of the top portion 42 and, thus, vertically below the separation wall 46, when installed. The push button opening may be sized to accommodate a push button 60 sliding within the push button opening. Push button 60 may have a similar structure to push button 20 described above. Push button 60 may comprise a button head designed to extend outward from the top portion 42 and a button body extending from the button head, the button body designed to be positioned within the bottom interior region of the top portion 42. As shown in, for example, FIG. 13, the push button body may comprise a narrow stem extending from the push button head, wherein the narrow stem may comprise an upper edge with raised outer walls, defining a push button slot 60A. When in use, the push button slot 60A may accommodate or slidably engage with the central lip on the separation wall, allowing the push button 60 to slide along a length of a bottom of the separation wall 46. A Pair of tabs may each extend substantially perpendicularly outward from a distal end of the stem, wherein each of the pair of tables may be substantially parallel with a surface of the push button head proximate to the stem. Each of the pair of tabs may comprise a slotted peg 66 extending outward therefrom and toward the button head. An O-ring 68 may encircle a shaft of the slotted peg 66, such that the O-ring 68 is positioned between a head of the slotted peg 66 and the tab.

Figures 11, 12:
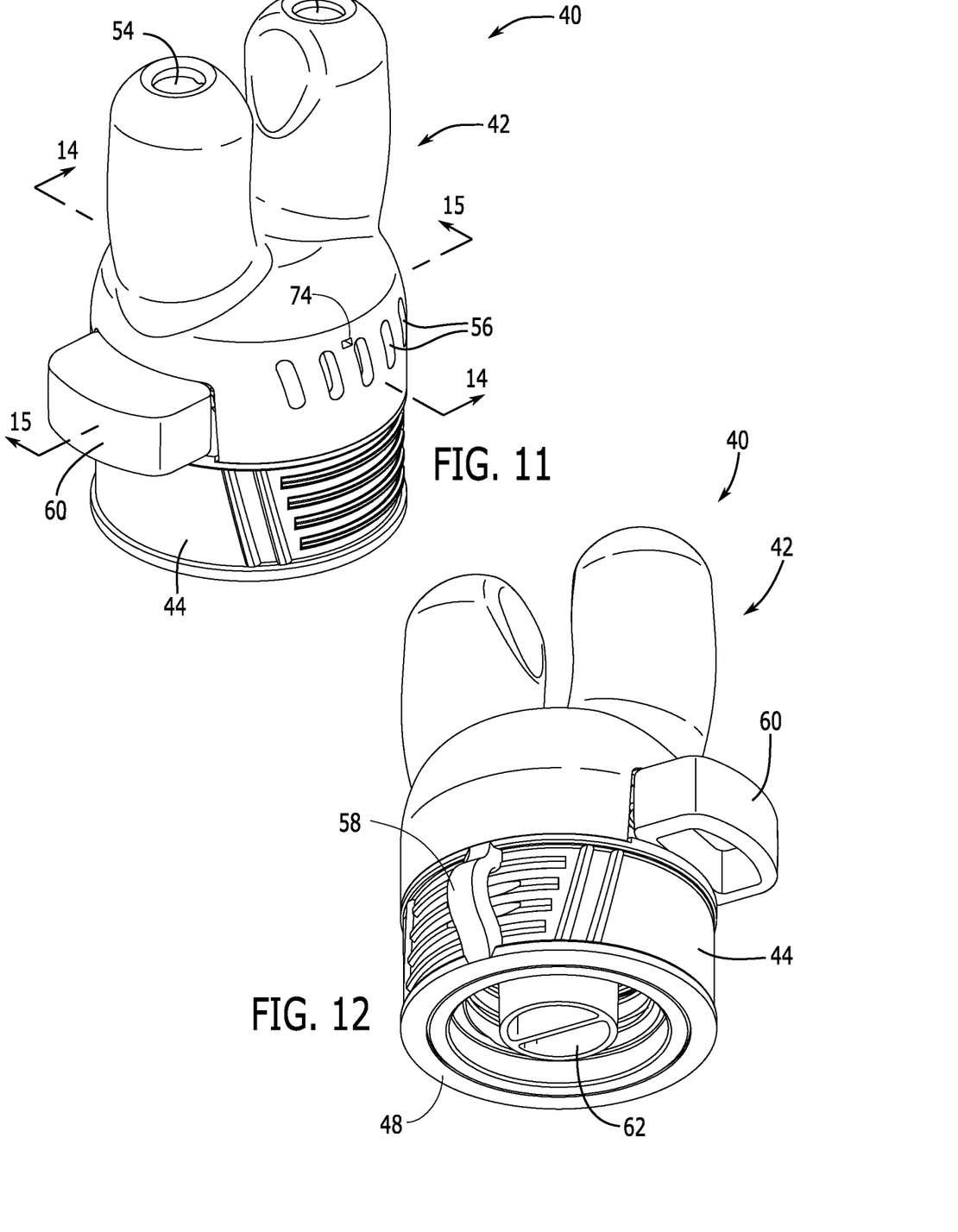
FIG. 11 is a top perspective view of one embodiment of the present disclosure.
FIG. 12 is a bottom perspective view of one embodiment of the present disclosure.

As shown in FIGS. 12 and 13, the bottom portion 44 of the cap body 40 may include a substantially cylindrical body with a first open end and a second closed end. The first open end may, similar to bottom portion 12B, include threads. Alternatively, as shown in FIG. 13, a threaded insert 48 may be positioned and secured within the bottom portion 44, wherein the threaded insert 48 may comprise interior threads designed to removably engage with threads on the neck of an aroma bottle 24. In some embodiments, a gasket 52 and a flange washer 50 may also be positioned between a top edge of the threaded insert 48 and the interior surface of the closed end of the bottom portion 44, wherein the gasket 52 and the flange washer 50 may, together, help ensure a sealed connection when the bottom portion 44 is engaged with the aroma bottle 24. As shown in the Figures, a dual section airflow tube 62 may be concentrically aligned with and attached to the closed end of the bottom portion 44, wherein the dual section airflow tube 62 is designed to extend to the open end of the bottom portion 44.

The dual section airflow tube 62 may have a structure similar to (or even identical to) the dual section airflow tube 22 described above. Specifically, the dual section airflow tube 62 may comprise a tube with a divider extending the length thereof, thus dividing the tube 62 into two airflow portions.

As shown in FIG. 13, the closed end of the bottom portion 44 may comprise a pair of valve protrusions extending upward therefrom, wherein each of the valve protrusions may be positioned on a respective opening in the closed end, wherein the first opening aligns with a first half of the dual section airflow tube 62 and the second opening aligns with a second half of the dual section airflow tube 62. Each valve protrusion may be substantially square or rectangular shaped with a respective channel 70 extending therein, wherein the channel 70 extends from a side surface down through a bottom surface, such that the exterior of the closed end is in fluid communication with the dual section airflow tube. The channels 70 may be sized to accommodate insertion of the respective slotted peg 66 and O-ring 68 therein. Thus, in embodiments, the push button 60 may be sandwiched between the top portion 42 and the bottom portion 44 of the cap body 40, wherein the stem of the push button 60 may be positioned between the pair of valve protrusions and movement of the push button 60 may cause the slotted pegs 66 to engage and disengage with the channels 70 in the valve protrusions.

As shown in FIG. 13, the bottom portion 44 may further comprise a pair of springs 30, wherein each spring 30 is attached to a surface of the valve protrusion opposite the channel 70 and is, thus, positioned between an edge of the valve protrusion and the push button head. As such, the springs 30 may force the push button 60 outward with respect to an interior of the cap body 40, causing the slotted pegs 66 and O-rings 68 to engage with the channel 70, thus blocking airflow between the dual section airflow tube 62 and the top portion 42 of the cap body 40. When the push button 60 is pressed toward the interior of the cap body 40, the slotted pegs 66 and O-rings 68 are disengaged from the channels 70, thus allowing airflow between the dual section airflow tube 62 and the top portion 42 of the cap body 12.

Figure 15:
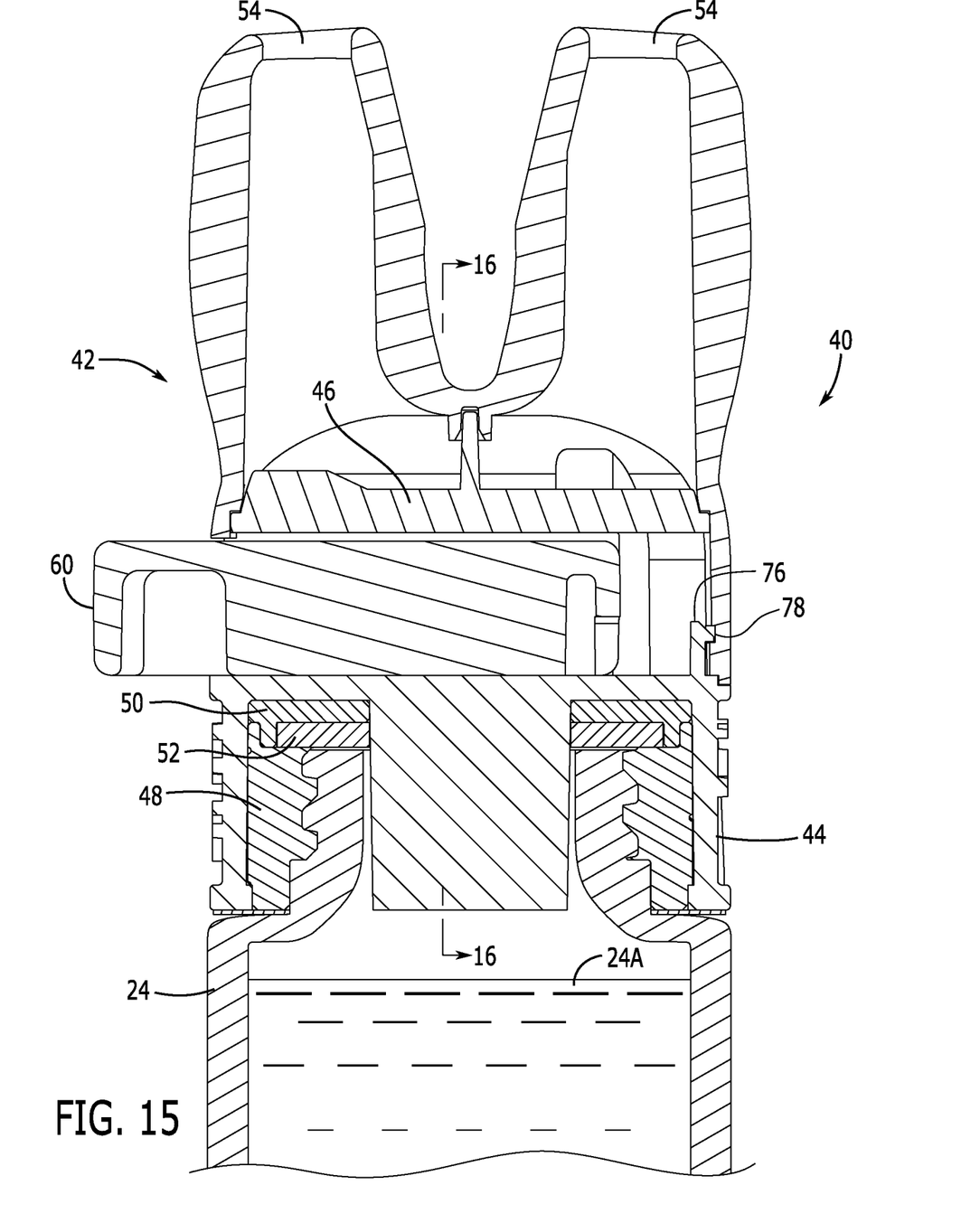
FIG. 15 is a cross-sectional view of one embodiment of the present disclosure, taken along line 15-15 in FIG. 11.
Figure 17:
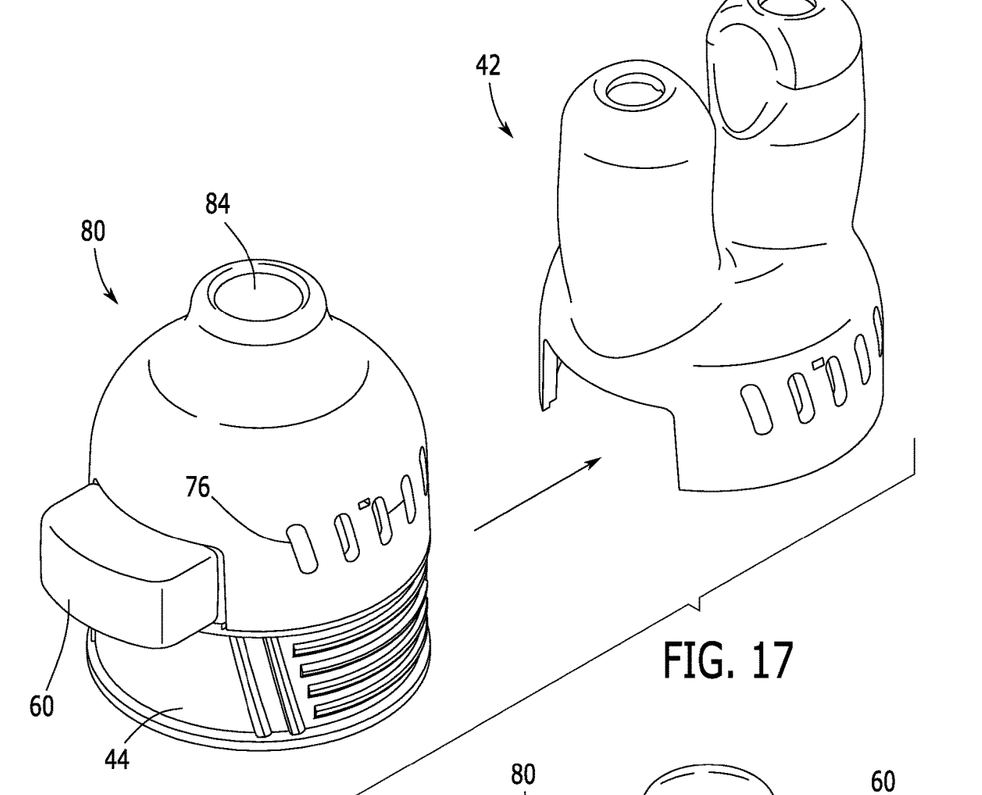
FIG. 17 is a top perspective view of one embodiment of the present disclosure, showing the switching of a single-nostril cap with a double-nostril cap.

As shown in FIGS. 14 and 15, the exterior surface of the closed end of the bottom portion 44 may further comprise a plurality of retention tabs 76 designed to engage with bottom clip slots 78 on an interior wall of the bottom region of the top portion 42 of the cap body 40. As such, the top portion 42 may be attached to the bottom portion 44 using such clips. In an alternate embodiment, the top portion may comprise a single nozzle top portion 80, as shown in FIG. 17, wherein the single nozzle top portion 80 may have the same structure as the double nozzle top portion 42, but for including a single nozzle and opening 84 rather than the pair of nozzle extension and openings, as shown in FIGS. 17 and 18.

Figure 18:
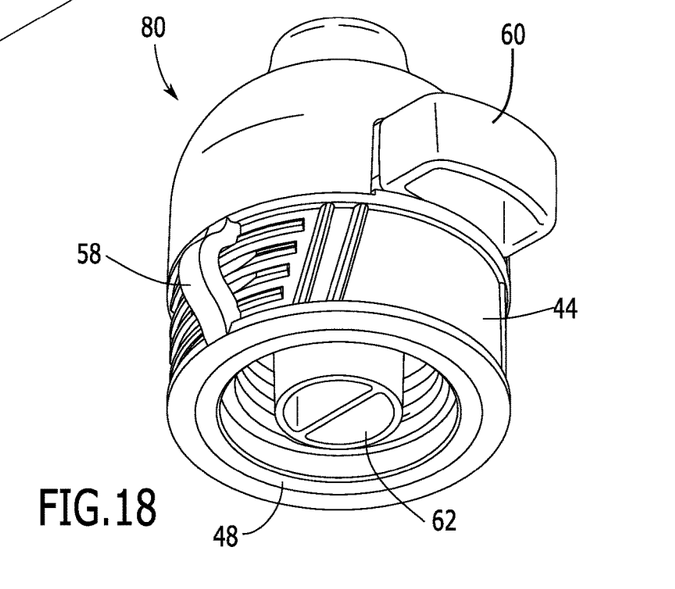
FIG. 18 is a bottom perspective view of one embodiment of the present disclosure.

In any embodiment of the cap body, the cap body may further comprise a necklace loop 58 extending from a surface of the cap body, such as from the bottom portion 44, as shown in FIG. 18.

To use the device of the present disclosure, a user may attach the sniffing cap device to the desired aroma bottle 24 with an aroma liquid 24A therein. The user may place his or her nostril(s) over the nozzle opening(s) in the top portion of the cap body. The user may then press the push button, opening airflow throughout the device. When the user inhales, air 34A may flow into the air vents, down through a first section of the dual section airflow tube and mix with the liquid aroma 24A in the bottle 24. The combine scent may then flow up through the second section of the dual section airflow tube, into the interior of the top portion and out through the nozzle opening(s) to the user's nostril(s). The user may then release the push button, causing the airflow to again be blocked. As such, the device of the present disclosure provides for regulated access to the aroma while simultaneously preventing or reducing the likelihood of unnecessary evaporation and accidental spillage.

The components of the device of the present disclosure may be made of any suitable materials, wherein the dimensions of the components may vary depending on, for example, the bottle to which it is being attached. Additionally, the positioning of the nozzle opening(s) may vary to accommodate easy sniffing from varying angles, such as while laying down. In some embodiments, the nozzle opening(s) may be modified for mouth inhalation. As shown in FIGS. 1-10, many of the components may be manufactured as a single integral part while, as shown in FIGS. 11-18, the components may be individually manufactured and then individually attached to one another. The material from which the device of the present disclosure is made is not particularly limited.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

What is claimed is:

1. A sniffing cap for an aroma bottle providing for regulated access to an aroma within the aroma bottle, the sniffing cap comprising
a cap body comprising:
a top cap portion comprising at least one nozzle opening designed to be placed against a user's nostril and air vents extending through a side surface of the top cap portion, the nozzle opening and the air vents being separated by an internal partition; and
a bottom cap portion attached to the top cap portion, the bottom cap portion designed to removably engage with the aroma bottle; and
a push button positioned between the top cap portion and the bottom cap portion, the push button including a push button body configured to engage and disengage with channels in the cap body, the push button comprising:
a button head designed to extend outward from the cap body; and
a button body extending from the button head, the button body designed to be positioned within an interior region of the cap body, wherein the button body comprises:
a stem extending from the button head, the stem comprising an upper edge with outer raised walls, defining a push button slot;
a pair of tabs extending outward from a distal end of the stem;
a first slotted peg extending outward from a first tab of the pair of tabs toward the button head; and
a second slotted peg extending outward from a second tab of the pair of tabs toward the button head,
wherein:
the push button is designed to slide from a first configuration to a second configuration;
the first configuration blocks airflow through the channels and, thus, the cap body; and
the second configuration allows for airflow through the channels and, thus, the cap body.

2. The sniffing cap of claim 1, wherein the internal partition comprises a central lip extending from a bottom surface thereof; and the push button slot is sized to accommodate the central lip therein, such that the push button is slidably engaged with the internal partition.

3. The sniffing cap of claim 1, further comprising:
a first O-ring encircling a shaft of the first slotted peg; and
a second O-ring encircling a shaft of the second slotted peg.

4. The sniffing cap of claim 1, wherein:
the at least one nozzle opening comprises a pair of nozzle openings; and
the top cap portion comprises:
a dome shaped outer wall with an open bottom;
a pair of nozzle extensions protruding from a surface of the outer wall, wherein each nozzle extension includes a respective nozzle opening of the pair of nozzle openings extending therethrough.

5. The sniffing cap of claim 1, wherein the internal partition is a member selected from the group consisting of an integrated internal partition and a removably attached separation wall.

6. The sniffing cap of claim 1, further comprising a dual section airflow tube extending from the bottom cap portion.

7. The sniffing cap of claim 6, wherein the bottom portion comprises:
a substantially cylindrical body with a first open end and a second closed end;
internal threads positioned in the first open end, the internal threads configured to engage with threads on a neck of the aroma bottle;
the dual section airflow tube concentrically positioned within the first open end and extending from an interior surface of the second closed end;
a first opening and a second opening extending through the second closed end, the first opening aligning with a first half of the dual section airflow tube and the second opening aligning with a second half of the dual section airflow tube;

a pair of valve protrusions extending upward from an exterior surface of the second closed end, each valve protrusion of the pair of valve protrusions positioned on a respective opening of the first opening and the second opening; and a first channel extending through a first valve protrusion of the pair of valve protrusions, and a second channel extending through a second valve protrusion of the pair of valve protrusions, such that the exterior of the second closed end is in fluid communication with the dual section airflow tube, wherein the first channel and the second channel are the channels in the cap body with which the push button is configured to engage and disengage.

8. The sniffing cap of claim 6, wherein the dual section airflow tube comprises a tube with at least one divider extending the length thereof, thus dividing the dual section airflow tube into at least two airflow portions.

9. A sniffing cap for an aroma bottle providing for regulated access to an aroma within the aroma bottle, the sniffing cap comprising a cap body comprising:
  a top cap portion comprising at least one nozzle opening designed to be placed against a user's nostril and air vents extending through a side surface of the top cap portion, the nozzle opening and the air vents being separated by an internal partition; and
  a bottom cap portion attached to the top cap portion, the bottom cap portion designed to removably engage with the aroma bottle;
a push button positioned between the top cap portion and the bottom cap portion, the push button including a push button body configured to engage and disengage with channels in the cap body; and
a dual section airflow tube extending from the bottom cap portion, wherein:
  the push button is designed to slide from a first configuration to a second configuration;
  the first configuration blocks airflow through the channels and, thus, the cap body;
  the second configuration allows for airflow through the channels and, thus, the cap body;
  the bottom portion comprises:
    a substantially cylindrical body with a first open end and a second closed end;
    internal threads positioned in the first open end, the internal threads configured to engage with threads on a neck of the aroma bottle;
    the dual section airflow tube concentrically positioned within the first open end and extending from an interior surface of the second closed end;
    a first opening and a second opening extending through the second closed end, the first opening aligning with a first half of the dual section airflow tube and the second opening aligning with a second half of the dual section airflow tube;
  a pair of valve protrusions extending upward from an exterior surface of the second closed end, each valve protrusion of the pair of valve protrusions positioned on a respective opening of the first opening and the second opening; and
  a first channel extending through a first valve protrusion of the pair of valve protrusions, and a second channel extending through a second valve protrusion of the pair of valve protrusions, such that the exterior of the second closed end is in fluid communication with the dual section airflow tube, wherein the first channel and the second channel are the channels in the cap body with which the push button is configured to engage and disengage.

* * * * *